United States Patent
Almirante et al.

(10) Patent No.: US 10,047,047 B2
(45) Date of Patent: Aug. 14, 2018

(54) NITRIC OXIDE DONATING DERIVATIVES OF LATANOPROST FREE ACID

(71) Applicant: Nicox S.A., Sophia Antipolis—Valbonne (FR)

(72) Inventors: Nicoletta Almirante, Milan (IT); Laura Storoni, Cesano Maderno (IT); Elena Bastia, Milan (IT); Stefania Brambilla, Merone (IT); Francesco Impagnatiello, Milan (IT)

(73) Assignee: NICOX S.A., Valbonne (FR)

( * ) Notice: Subject to any disclaimer, the term of this patent is extended or adjusted under 35 U.S.C. 154(b) by 0 days.

(21) Appl. No.: 15/561,919

(22) PCT Filed: Mar. 22, 2016

(86) PCT No.: PCT/EP2016/056224
§ 371 (c)(1),
(2) Date: Sep. 26, 2017

(87) PCT Pub. No.: WO2016/156104
PCT Pub. Date: Oct. 6, 2016

(65) Prior Publication Data
US 2018/0118676 A1    May 3, 2018

(30) Foreign Application Priority Data
Mar. 31, 2015 (EP) ................... 15162002

(51) Int. Cl.
| | | |
|---|---|---|
| *C07C 405/00* | (2006.01) | |
| *A61P 27/02* | (2006.01) | |
| *A61P 27/06* | (2006.01) | |
| *A61K 45/06* | (2006.01) | |
| *A61K 31/5575* | (2006.01) | |
| *A61K 9/00* | (2006.01) | |

(52) U.S. Cl.
CPC .......... *C07C 405/00* (2013.01); *A61K 9/0048* (2013.01); *A61K 31/5575* (2013.01); *A61K 45/06* (2013.01); *A61P 27/02* (2018.01); *A61P 27/06* (2018.01); *C07C 2601/08* (2017.05)

(58) Field of Classification Search
CPC ........ A61P 27/02; C07C 405/00; A61K 31/04
See application file for complete search history.

(56) References Cited

FOREIGN PATENT DOCUMENTS

| | | |
|---|---|---|
| WO | WO 2007/000641 A2 | 1/2007 |
| WO | WO 2009/136281 A1 | 11/2009 |

OTHER PUBLICATIONS

Impagnatiello, "A dual acting compound with latanoprost amide and nitric oxide releasing properties, shows ocular hypotensive effects in rabbits and dogs", Experimental Eye Research 93 (2011) 243-249.
International Search Report and Written Opinion issued in International Patent Application No. PCT/EP2016/056224.

*Primary Examiner* — Heidi Reese
(74) *Attorney, Agent, or Firm* — Arent Fox LLP

(57) ABSTRACT

The present invention relates to 15-nitrooxyderivatives of latanoprost and 15-nitrooxyderivatives of latanoprost free acid, their use for the treatment of glaucoma and ocular hypertension and formulation containing 15-nitrooxyderivatives of latanoprost and 15-nitrooxyderivatives of latanoprost free acid.

19 Claims, No Drawings

NITRIC OXIDE DONATING DERIVATIVES OF LATANOPROST FREE ACID

CROSS-REFERENCE TO RELATED APPLICATIONS

This application is a National Stage entry of International Application No.: PCT/EP2016/056224, filed Mar. 22, 2016, which claims priority to European Patent Application No. 15162002.8, filed Mar. 31, 2015. The disclosure of the priority applications are hereby incorporated in their entirety by reference.

The present invention relates to 15-nitrooxyderivatives of latanoprost and 15-nitrooxyderivatives of latanoprost free acid, their use for the treatment of glaucoma and ocular hypertension and formulation containing 15-nitrooxyderivatives of latanoprost or 15-nitrooxyderivatives of latanoprost free acid.

Latanoprost free acid and Latanoprost, both known compounds, are synthetic analogues of Prostaglandin $F_{2\alpha}$; the chemical name for latanoprost free acid is 17-phenyl-13,14-dihydro trinor Prostaglandin $F_{2\alpha}$ and the chemical name of Latanoprost is isopropyl ester of 17-phenyl-13,14-dihydro trinor prostaglandin $F_{2\alpha}$.

Glaucoma is a group of eye disorders leading to progressive damage to the optic nerve, and is characterized by loss of nerve tissue resulting in loss of vision. The most common form of glaucoma, primary open-angle glaucoma, is associated with an increase in the fluid pressure inside the eye. This increase in pressure may cause progressive damage to the optic nerve and loss of nerve fibers. Advanced glaucoma may even cause blindness. Glaucoma is the second leading cause of blindness in the U.S. It most often occurs in people over age 40, although a congenital or infantile form of glaucoma exists.

There are many types of glaucoma. The most common form of glaucoma, primary open-angle glaucoma, develops slowly and usually without any symptoms. It initially affects peripheral or side vision, but can advance to central vision loss. If left untreated, glaucoma can lead to significant loss of vision in both eyes, and may even lead to blindness.

A less common type of glaucoma, acute angle closure glaucoma, usually occurs abruptly due to a rapid increase of pressure in the eye.

Secondary glaucoma occurs as a result of an injury or other eye disease. It may be caused by a variety of medical conditions, physical injuries, and eye abnormalities. Infrequently, eye surgery can be associated with secondary glaucoma.

Normal-tension glaucoma, also known as low-tension glaucoma, is characterized by progressive optic nerve damage and visual field loss with normal intra ocular pressure (IOP) and may account for as many as one-third of the cases of open-angle glaucoma in U.S. Normal-tension glaucoma is thought to be, in part, due to poor blood flow to the optic nerve, which leads to death of the ganglion cells which carry impulses from the retina to the brain. A pressure lower than normal is necessary to prevent further visual loss.

The most common first line treatment of glaucoma is drug treatment. Several classes of drugs acting by different mechanisms are used as topically administered ocular therapy to lower IOP. These include beta adrenergic blockers (e.g., timolol), topical carbonic anhydrase inhibitors (e.g., dorzolamide), and alpha 2-adrenergic receptor agonists (e.g., brimonidine), all of which act primarily by decreasing the formation of aqueous humor within the eye. Pilocarpine and epinephrine are clinical agents that also lower IOP in glaucomatous eyes, but these drugs act principally by decreasing the resistance in the trabecular meshwork outflow channels. A third mechanism for lowering IOP in the primate eye is by increasing the outflow of aqueous humor via the uveoscleral route.

Prostaglandin analogs have met an increasing interest for glaucoma therapy as IOP-lowering substances which act primarily by increasing the uveoscleral outflow.

Recently, nitric oxide (NO)-donating prostaglandin derivatives have been studied as IOP-lowering compounds for the treatment of glaucoma and there are some reports on the studies. For example Journal of Ocular Pharmacology and Therapeutics (2010), 26(2), 125-131, Experimental Eye Research (2011), 93(3), 243-249 and Experimental Eye Research (2011), 93(3), 250-255 disclose the IOP lower effect of two NO donating latanoprost acid derivatives. The compound known as BOL-303259-X is now in clinical development for the treatment of primary open-angle glaucoma.

The drug therapies for glaucoma are sometimes associated with significant side effects, for example timolol and other topically applied beta blockers have been associated with asthma exacerbation, worsening congestive heart failure and, rarely heart block.

Pilocarpine may cause systemic cholinergic effects such as nausea, vomiting, sweating and cutaneous vasodilatation. $PGF_{2\alpha}$ and its esters are characterized by the occurrence of ocular side effects, primarily conjunctival hyperemia.

Patients with glaucoma need to continue treatment for the rest of their lives. Because the disease can progress, only by keeping eye pressure under control can continued damage to the optic nerve and continued loss of visual field be slowed or stopped.

Intraocular pressure is the primary risk factor for glaucoma and lowering IOP to prevent optic nerve injury is the only proven effective treatment (Kass M A, et al., Arch Ophthalmol, 2002, 120:701-703; The AGIS Investigators, Am J Ophthalmol, 2000, 130:429-440).

PCT publications WO 2005/068421, WO 2009/136281, WO 2007/000641 and WO 2007/0642 describe (NO)-donating prostaglandin derivatives with increased ocular hypotensive activity in particular WO 2009/136281 discloses 15-nitrooxyderivative of prostamides such as bimatoprost and latanoprost acid ethyl amide. Said compounds have been shown to have greater hypotensive efficacy than the parent compound. Latanoprost acid ethyl amide is distinguished from latanoprost in that the oxygen which is bonded to carbonyl group is replaced by a nitrogen bearing an ethyl group.

In spite of all the treatments evolved over decades as described above, there is still a need for new drugs for treatments and therapies for glaucoma and elevated intra ocular pressure.

Thus, this invention provides 15-nitrooxyderivatives of latanoprost and 15-nitrooxyderivatives of latanoprost free acid useful for the treatment of glaucoma and elevated intraocular pressure.

It has now been found that 15-nitrooxyderivatives of latanoprost and 15-nitrooxyderivatives of latanoprost free acid are efficacious and potent ocular hypotensive agents and therefore the 15-nitrooxyderivatives of latanoprost and 15-nitrooxyderivatives of latanoprost free acid of the present invention can be employed for treating ocular hypertension and glaucoma, in particular chronic open-angle glaucoma.

An embodiment of the invention relates to compounds of formula (I) or salts thereof (I)

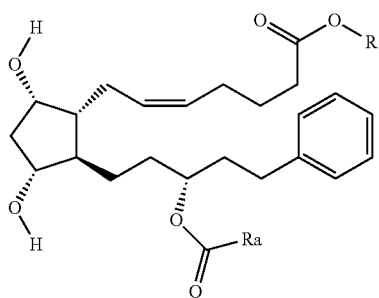

wherein

R is —CH(CH$_3$)$_2$ or H; preferably R is —CH(CH$_3$)$_2$;

Ra is selected from

A1):  —(CHR$^1$)—NH—(C=O)—(CH$_2$)$_m$—[O—(CH$_2$)$_n$]$_p$—(CH—ONO$_2$)$_q$—CH$_2$—ONO$_2$

A2):  —(CH$_2$)$_2$—NH—(C=O)—(CH$_2$)$_m$—[O—(CH$_2$)$_n$]$_p$—(CH—ONO$_2$)$_q$—CH$_2$—ONO$_2$

A3):  —(CH$_2$)$_m$—[O—(CH$_2$)$_n$]$_p$—(CH—ONO$_2$)$_q$—CH$_2$—ONO$_2$ wherein R$^1$ is —H or —CH$_3$, p is 1 or 0, q is 1 or 0, m is an integer ranging from 1 to 10; preferably m is from 1 to 6;

n is an integer ranging from 1 to 6; preferably n is 1 or 2.

Preferred linkers having structure A1 are below reported:

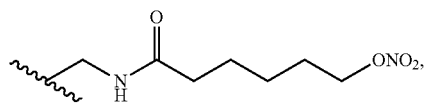

(1-A1)

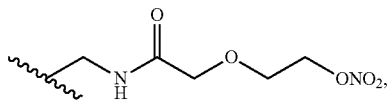

(2-A1)

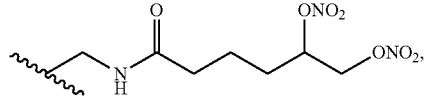

(3-A1)

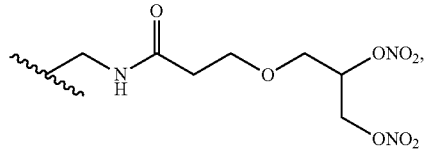

(4-A1)

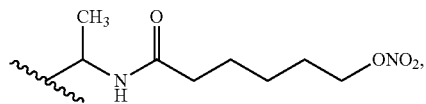

(5-A1)

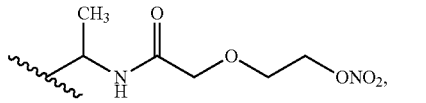

(6-A1)

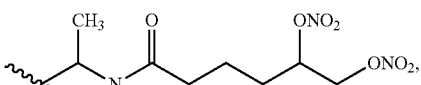

(7-A1)

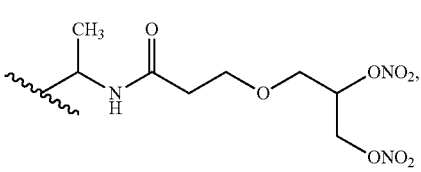

(8-A1)

preferred linkers having structure A2 are below reported:

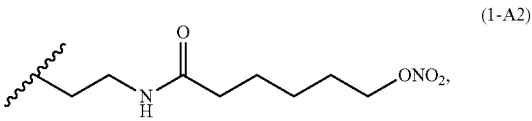

(1-A2)

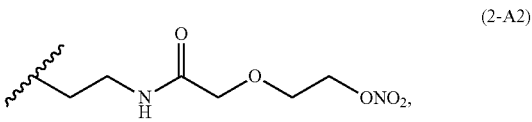

(2-A2)

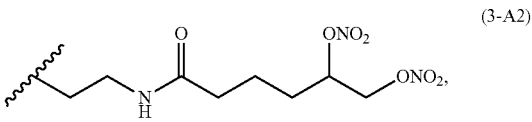

(3-A2)

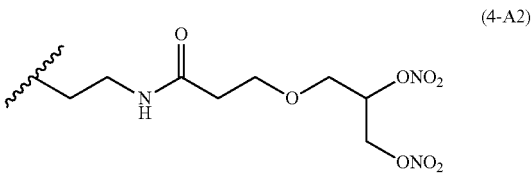

(4-A2)

preferred linkers having structure of the group A3 are below reported:

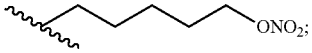

(1-A3)

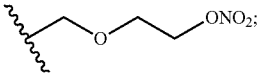

(2-A3)

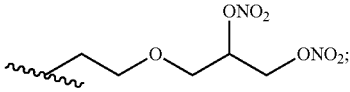

(3-A3)

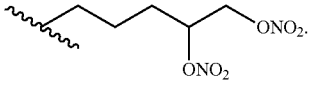

(4-A3)

Another embodiment of the invention relates to compounds of formula (I) wherein

R is —CH(CH$_3$)$_2$;

Ra is A1): —(CHR$^1$)—NH—(C=O)—(CH$_2$)$_m$—[O—(CH$_2$)$_n$]$_p$—(CH—ONO$_2$)$_q$—CH$_2$—ONO$_2$ wherein R$^1$ is —H or —CH$_3$, p is 1 or 0, q is 1 or 0, m is an integer ranging from 1 to 10; preferably m is from 1 to 6;

n is an integer ranging from 1 to 6; preferably n is 1 or 2.

Another embodiment of the invention relates to compounds of formula (I) wherein

R is —CH(CH$_3$)$_2$ and

Ra is selected from the following group of linkers having structure A1:

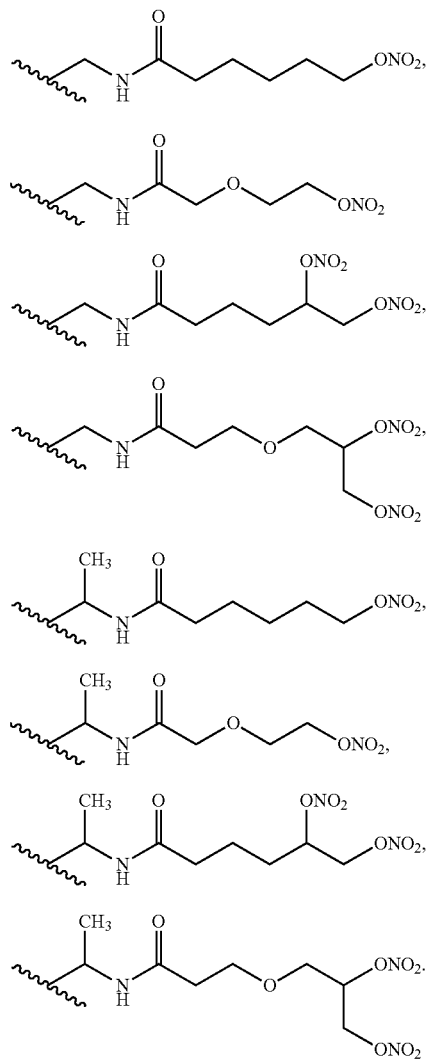

(1-A1)

(2-A1)

(3-A1)

(4-A1)

(5-A1)

(6-A1)

(7-A1)

(8-A1)

An embodiment of the invention relates to compounds of formula (I) wherein

R is —CH(CH$_3$)$_2$;

Ra is A2): —(CH$_2$)$_2$—NH—(C=O)—(CH$_2$)$_m$—[O—(CH$_2$)$_n$]$_p$—(CH—ONO$_2$)$_q$—CH$_2$—ONO$_2$ wherein p is 1 or 0, q is 1 or 0, m is an integer ranging from 1 to 10; preferably m is from 1 to 6;

n is an integer ranging from 1 to 6; preferably n is 1 or 2.

An embodiment of the invention relates to compounds of formula (I) wherein

R is —CH(CH$_3$)$_2$ and

Ra is selected from the following group of linkers having structure A2:

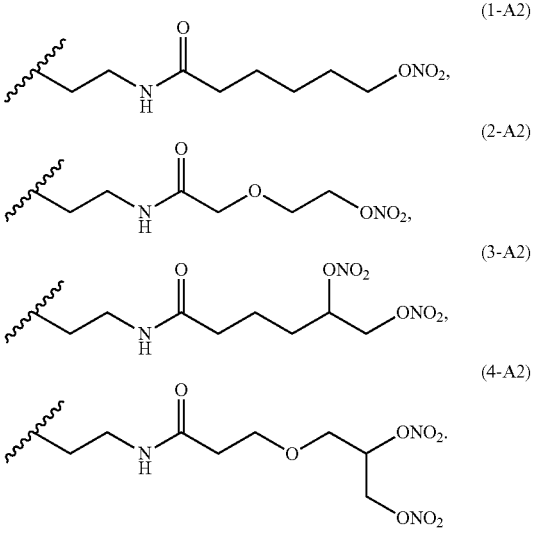

(1-A2)

(2-A2)

(3-A2)

(4-A2)

An embodiment of the invention relates to compounds of formula (I) wherein

R is —CH(CH$_3$)$_2$;

Ra is A3): —(CH$_2$)$_m$—[O—(CH$_2$)$_n$]$_p$—(CH—ONO$_2$)$_q$—CH$_2$—ONO$_2$ wherein p is 1 or 0, q is 1 or 0, m is an integer ranging from 1 to 10; preferably m is from 1 to 6;

n is an integer ranging from 1 to 6; preferably n is 1 or 2.

An embodiment of the invention relates to compounds of formula (I) wherein

R is —CH(CH$_3$)$_2$ and

Ra is selected from the following group of linkers having structure A3:

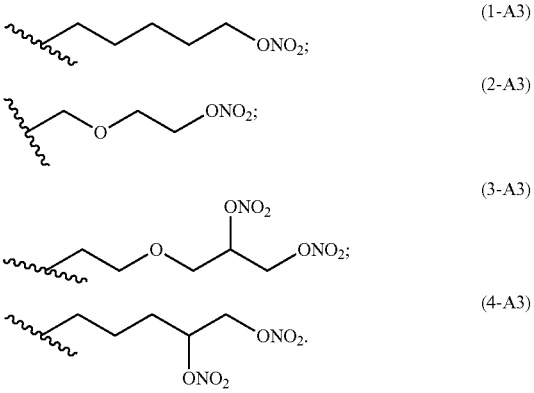

(1-A3)

(2-A3)

(3-A3)

(4-A3)

Another embodiment of the invention relates to compounds of formula (I) or salts thereof wherein R is —H;

Ra is A1): —(CHR$^1$)—NH—(C=O)—(CH$_2$)$_m$—[O—(CH$_2$)$_n$]$_p$—(CH—ONO$_2$)$_q$—CH$_2$—ONO$_2$ wherein R¹ is —H or —CH₃,
p is 1 or 0,
q is 1 or 0,
m is an integer ranging from 1 to 10; preferably m is from 1 to 6;
n is an integer ranging from 1 to 6; preferably n is 1 or 2.

Another embodiment of the invention relates to compounds of formula (I) wherein

R is —H and
Ra is selected from the following group of linkers having structure A1:

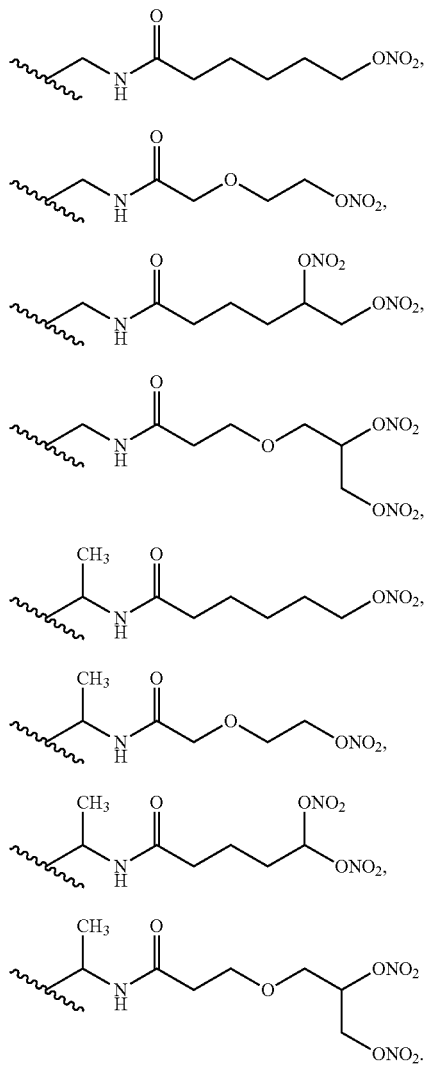

An embodiment of the invention relates to compounds of formula (I) or salts thereof wherein R is —H;
Ra is A2): —(CH₂)₂—NH—(C═O)—(CH₂)ₘ—[O—(CH₂)ₙ]ₚ—(CH—ONO₂)_q—CH₂—ONO₂
wherein
p is 1 or 0,
q is 1 or 0,
m is an integer ranging from 1 to 10; preferably m is from 1 to 6;
n is an integer ranging from 1 to 6; preferably n is 1 or 2.

An embodiment of the invention relates to compounds of formula (I) wherein

R is —H and
Ra is selected from the following group of linkers having structure A2:

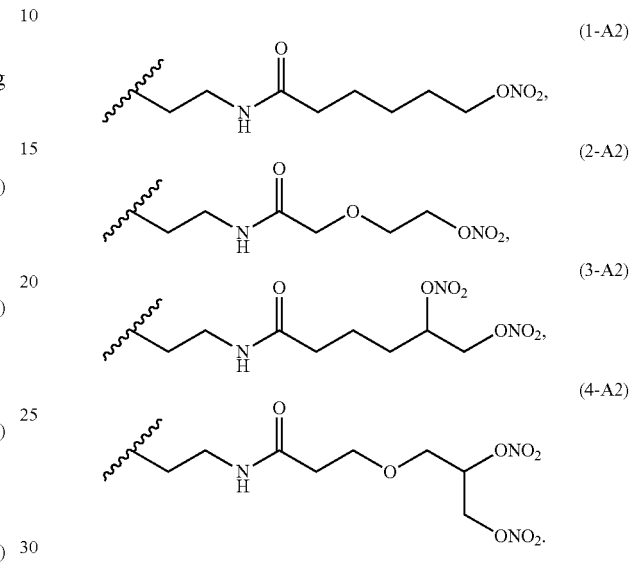

An embodiment of the invention relates to compounds of formula (I) or salts thereof wherein R is —H;
Ra is A3): —(CH₂)ₘ—[O—(CH₂)ₙ]ₚ—(CH—ONO₂)_q—CH₂—ONO₂
wherein
p is 1 or 0,
q is 1 or 0,
m is an integer ranging from 1 to 10; preferably m is from 1 to 6;
n is an integer ranging from 1 to 6; preferably n is 1 or 2.

An embodiment of the invention relates to compounds of formula (I) wherein

R is —H and
Ra is selected from the following group of linkers having structure A3:

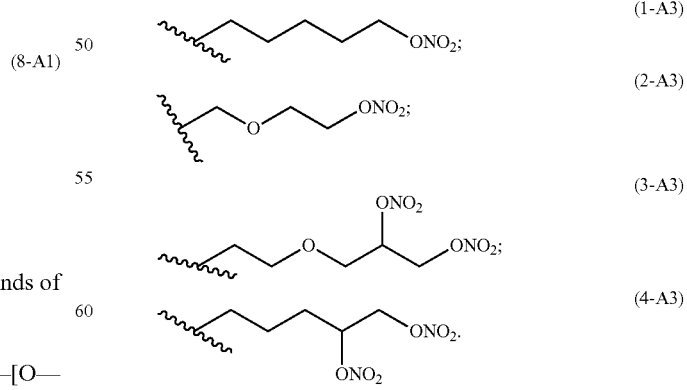

Another embodiment of the inventions relates to a compound of formula (I) selected from the following group of compounds:

(Z)-isopropyl 7-((1R,2R,3R,5S)-3,5-dihydroxy-2-((R)-3-(3-(6-(nitrooxy)hexanamido) propanoyloxy)-5-phenylpentyl)cyclopentyl)hept-5-enoate (Compound (1))

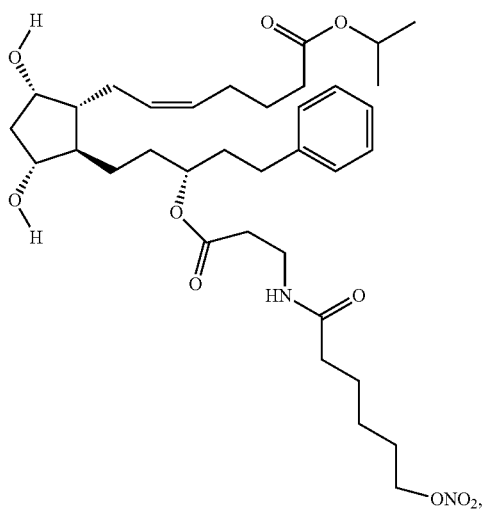

(Z)-isopropyl 7-((1R,2R,3R,5S)-3,5-dihydroxy-2-((R)-3-(3-(2-(2-(nitrooxy)ethoxy) acetamido)propanoyloxy)-5-phenylpentyl)cyclopentyl)hept-5-enoate (Compound (3))

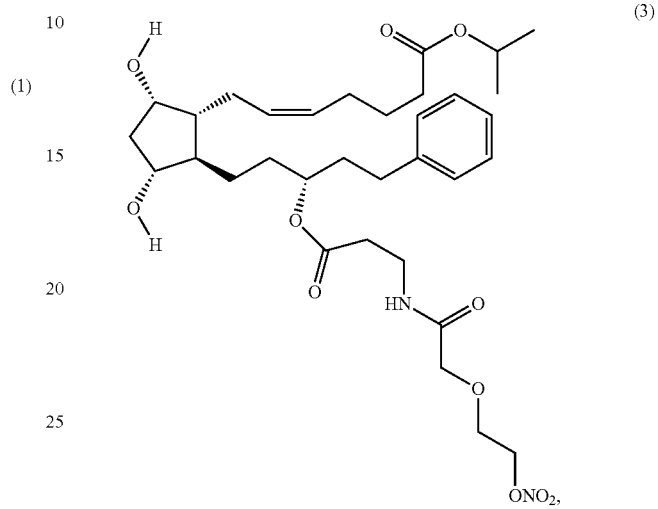

(Z)-isopropyl 7-((1R,2R,3R,5S)-2-((3R)-3-(3-(5,6-bis(nitrooxy)hexanamido) propanoyloxy)-5-phenylpentyl)-3,5-dihydroxycyclopentyl)hept-5-enoate (Compound (2))

(Z)-isopropyl 7-((1R,2R,3R,5S)-2-((3R)-3-(3-(3-(2,3-bis(nitrooxy)propoxy) propanamido)propanoyloxy)-5-phenylpentyl)-3,5-dihydroxycyclopentyl)hept-5-enoate (Compound (4))

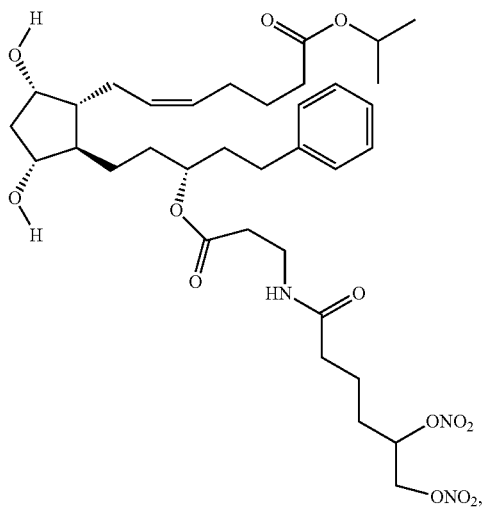

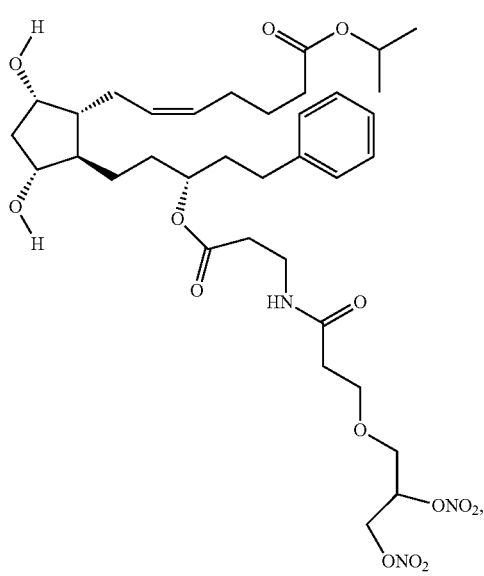

(Z)-isopropyl 7-((1R,2R,3R,5S)-3,5-dihydroxy-2-((R)-3-(2-(6-(nitrooxy)hexanamido) acetoxy)-5-phenylpentyl)cyclopentyl)hept-5-enoate (Compound (5))

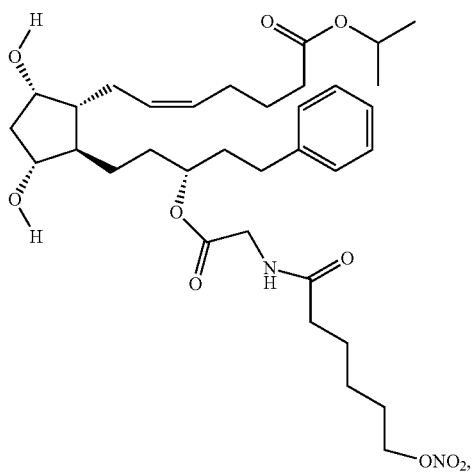

(Z)-isopropyl 7-((1R,2R,3R,5S)-2-((3R)-3-(2-(5,6-bis(nitrooxy)hexanamido)acetoxy)-5-phenylpentyl)-3,5-dihydroxycyclopentyl)hept-5-enoate (Compound (6))

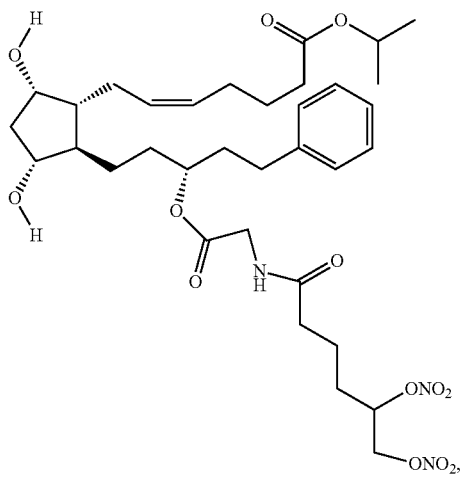

(Z)-isopropyl 7-((1R,2R,3R,5S)-3,5-dihydroxy-2-((R)-3-(2-(2-(2-(nitrooxy)ethoxy) acetamido)acetoxy)-5-phenylpentyl)cyclopentyl)hept-5-enoate (Compound (7))

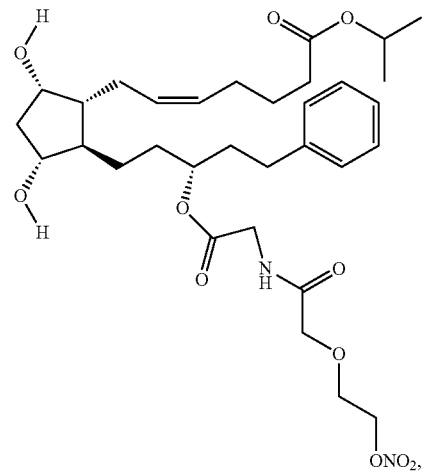

(Z)-isopropyl 7-((1R,2R,3R,5S)-2-((3R)-3-(2-(3-(2,3-bis(nitrooxy)propoxy) propanamido)acetoxy)-5-phenylpentyl)-3,5-dihydroxycyclopentyl)hept-5-enoate (Compound (8))

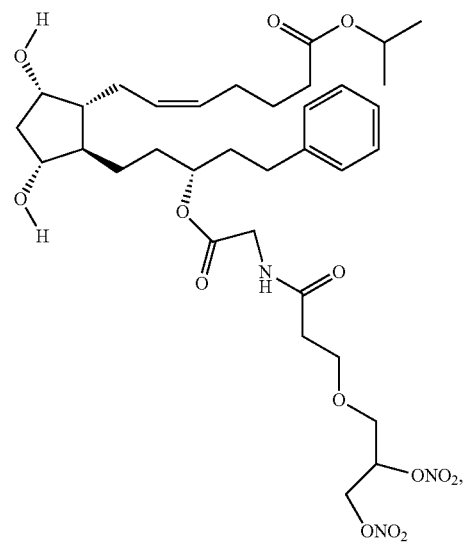

(Z)-isopropyl 7-((1R,2R,3R,5S)-3,5-dihydroxy-2-((R)-3-(6-(nitrooxy)hexanoyloxy)-5-phenylpentyl)cyclopentyl)hept-5-enoate (Compound (9))

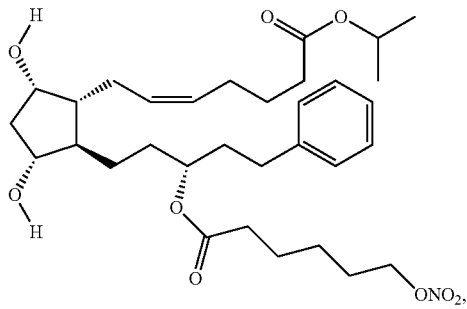

(Z)-isopropyl 7-((1R,2R,3R,5S)-2-((3R)-3-(5,6-bis(nitrooxy)hexanoyloxy)-5-phenylpentyl)-3,5-dihydroxycyclopentyl)hept-5-enoate (Compound (10))

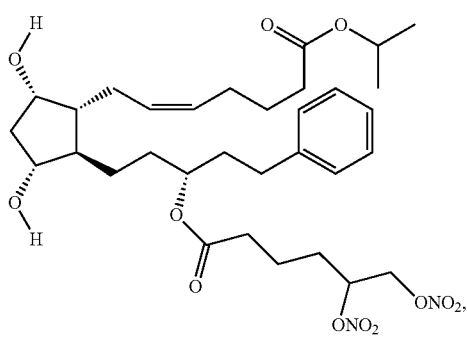

(Z)-isopropyl 7-((1R,2R,3R,5S)-3,5-dihydroxy-2-((R)-3-(2-(2-(nitrooxy)ethoxy)acetoxy)-5-phenylpentyl)cyclopentyl)hept-5-enoate (Compound (11))

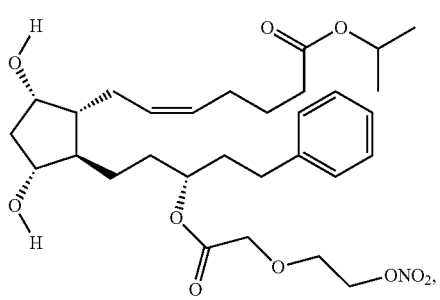

(Z)-isopropyl 7-((1R,2R,3R,5S)-2-((3R)-3-(3-(2,3-bis(nitrooxy)propoxy)propanoyloxy)-5-phenylpentyl)-3,5-dihydroxycyclopentyl)hept-5-enoate (Compound (12))

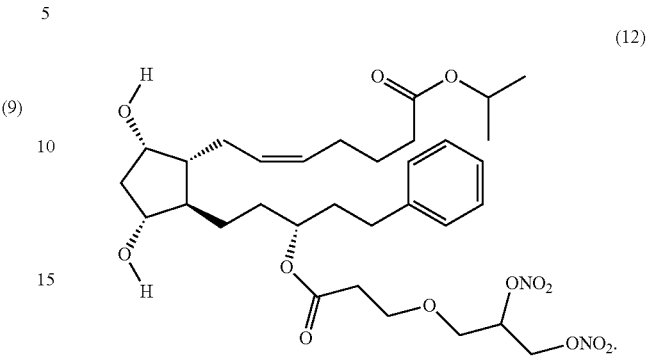

The term "salt" has the meaning normally understood by those of ordinary skill in the art. Pharmaceutically acceptable salts of acidic functional groups may be related to organic or inorganic bases. The salt may be a mono or polyvalent ion. Of particular interest are the inorganic ions, lithium, sodium, potassium, calcium, and magnesium. Organic salts may be made with amines, particularly ammonium salts such as mono-, di- and trialkyl amines or ethanol amines.

Included within the scope of the present invention are the individual enantiomers of the compounds of formula (I), as well as their racemic and non-racemic mixtures.

Another embodiment provides the use of compound of formula (I) for treating ocular hypertension.

Another embodiment provides the use of compound of Formula (I) for treating glaucoma in particular primary open angle glaucoma, normal intraocular tension glaucoma, pseudoexfoliation glaucoma, acute angle-closure glaucoma, chronic closed angle glaucoma.

The compound may be provided as part of a pharmaceutical composition as described therein.

In forming the compositions for topical administration, the compounds of the present invention are generally formulated as between about 0.00003 to about 3 percent by weight (wt %) solutions in water at a pH between 4.5 to 8.0. The compounds are preferably formulated as between about 0.003 to about 1 wt % and, most preferably, between about 0.004 and about 0.3 wt %.

In another aspect, there is provided a topical ocular pharmaceutical composition. The pharmaceutical composition includes a compound of Formula (I) or salts thereof and a pharmaceutically acceptable excipient. Acceptable excipients may include preservatives, dissolving agents and viscosity agents.

Suitable preservatives include: benzalkonium chloride, thimerosal, chlorobutanol, methyl paraben, propyl paraben, phenylethyl alcohol, edetate disodium, sorbic acid or other agents known to those skilled in the art. Such preservatives are typically employed at a concentration between about 0.001% and about 1.0% by weight. Dissolving agents include: polysorbates for example polyoxyethylene sorbitan monolaurate, and polyoxyethylene sorbitan monooleate for polysorbate 80, polyoxylated castor oil such as polyoxyethylene hydrogenated castor oil 40 and polyoxyethylene hydrogenated castor oil 60, polyoxyl stearate, macrogol, propyleneglycol; or other agents known to those skilled in the art. The dissolving agent may be used solely or in combination with one or more other dissolving agents.

Viscosity agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose or other agents known to those skilled in the art.

The ophthalmic composition of the present invention may further contain other additives. Examples of the additives may include osmotic adjusting agents such as sodium chloride, potassium chloride, calcium chloride, sodium bicarbonate, sodium carbonate, magnesium sulfate, sodium hydrogen phosphate, sodium dihydrogen phosphate, dipotassium hydrogen phosphate, borax, sodium hydroxide, hydrochloric acid, isosorbitol, propylene glycol, mannitol, sucrose and glucose; buffering agents such as sodium monohydrogen phosphate and sodium dihydrogen phosphate.

The compound of the present invention can also be used in combination with the following classes of drugs: Beta-adrenergic antagonists including carteolol, levobunolol, metipranolol, timolol hemihydrate; Adrenergic agonists including non-selective adrenergic agonists such as epinephrine borate, epinephrine hydrochloride, and dipivefrin; and Alpha$_2$-selective adrenergic agonists such as apraclonidine and the like; Carbonic Anhydrase Inhibitors including such as acetazolamide, dichlorphenamide, methazolamide, brinzolamide, dorzolamide; Cholinergic agonists such as carbachol, pilocarpine hydrochloride, pilocarbine nitrate, pilocarpine; Cholinesterase inhibitors such as demecarium, echothiophate, physostigmine.

Another embodiment of the invention relates to a composition comprising a compound of formula (I) and at least another active agent selected from the following classes of drugs: Beta-adrenergic antagonists including carteolol, levobunolol, metipranolol, timolol hemihydrate; Adrenergic agonists including non-selective adrenergic agonists such as epinephrine borate, epinephrine hydrochloride, and dipivefrin; and Alpha$_2$-selective adrenergic agonists such as apraclonidine and the like; Carbonic Anhydrase Inhibitors including such as acetazolamide, dichlorphenamide, methazolamide, brinzolamide, dorzolamide; Cholinergic agonists such as carbachol, pilocarpine hydrochloride, pilocarbine nitrate, pilocarpine; Cholinesterase inhibitors such as demecarium, echothiophate, physostigmine.

General Synthesis

1) The compound of formula (I) wherein R is —CH(CH$_3$)$_2$ and Ra is selected from the groups A1), A2) or A3):
A1): —(CHR$^1$)—NH—(C=O)—(CH$_2$)$_m$—[O—(CH$_2$)$_n$]$_p$—(CH—ONO$_2$)$_q$—CH$_2$—ONO$_2$
A2): —(CH$_2$)$_2$—NH—(C=O)—(CH$_2$)$_m$—[O—(CH$_2$)$_n$]$_p$—(CH—ONO$_2$)$_q$—CH$_2$—ONO$_2$
A3): —(CH$_2$)$_m$—[O—(CH$_2$)$_n$]$_p$—(CH—ONO$_2$)$_q$—CH$_2$—ONO$_2$ wherein:
R$^1$, m, n, p and q are as above defined;
can be prepared by reacting a compound of formula (II), wherein Ra is as above defined, with methanol or other alcohols:

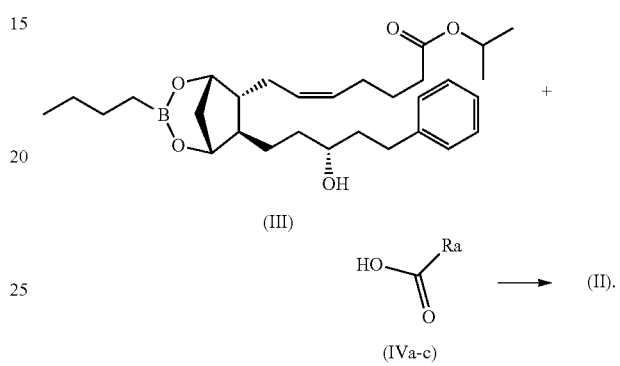

Compounds of formula (II), wherein Ra is as above defined, can be generally prepared by reacting a compound of formula (III) with compounds of formula (IVa-c):

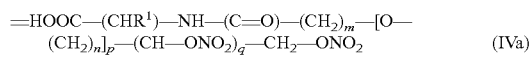
(IVa)

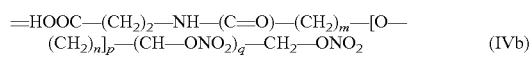
(IVb)

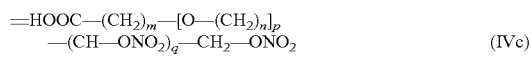
(IVc)

as depicted in the below reported scheme:

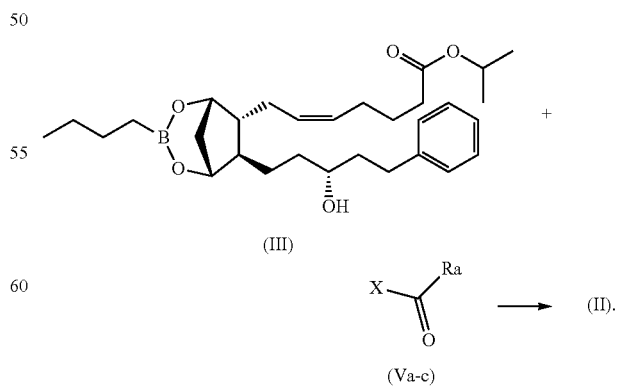

The reaction is carried out in a aprotic polar/non polar solvent such as THF, DMF or CH$_2$Cl$_2$, in presence of DCC, EDAC, HBTU, HATU or other coupling reagents, in presence of catalytic amount of DMAP at temperature ranging from –0° C. to 80° C.

Alternatively, the compounds of formula (II) can be generally prepared by reacting a compound of formula (III) with compounds of formula (Va-c):

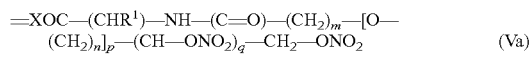
(Va)

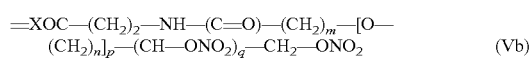
(Vb)

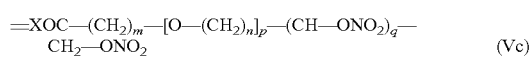
(Vc)

wherein X is —Cl, p-nitrophenoxy, pentafluorophenoxy or 2,5-pyrrolidinedione, 1-oxy, as depicted in the below reported scheme:

When X=—Cl, the reaction is carried out in presence of a base such as DMAP, pyridine or triethylamine or K$_2$CO$_3$, $Cs_2CO_3$ in an aprotic/non polar solvent such as THF, DMF or $CH_2Cl_2$, at a temperature ranging from −20° C. to 60° C.

When X is selected from p-nitrophenoxy, pentafluorophenoxy or 2,5-pyrrolidinedione, 1-oxy, the reaction is carried out in a aprotic polar/non polar solvent such as THF, DMF or $CH_2Cl_2$, in presence of DMAP at temperature ranging from 0° C. to 80° C.

The compound of formula (III) is known in the literature (see WO2012/139164-A1) and can be also prepared by reacting latanoprost with butylboronic acid following a general procedure reported in Organic Syntheses, Coll. Vol. 10, p. 613 (2004).

Compounds of formula (IVa) and (IVb) can be prepared by basic hydrolysis of correspondent compounds of formula (VIa) and (VIb):

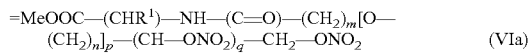
(VIa)

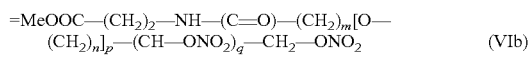
(VIb)

wherein $R^1$, m, n, p, q are as above defined.

Compounds of formula (VIa) and (VIb) can be prepared by reacting compounds (IVc) or (Vc) with commercially available compounds of formula (VIIa) or (VIIb):

=MeOOC—(CHR$^1$)—NH$_2$ (VIIa)

=MeOOC—(CH$_2$)$_2$—NH$_2$ (VIIb)

wherein $R^1$ is as above defined, according to methods well known in the art.

Alternatively compounds of formula (IVa) and (IVb) can be prepared by acid hydrolysis of correspondent compounds of formula (VIc) and (VId):

(VIc)

(VId)

wherein $R^1$, m, n, p, q are as above defined.

Compounds of formula (VIc) and (VId) can be prepared by reacting compounds (IVc) or (Vc) with commercially available compounds of formula (VIIc) or (VIId):

=t-ButOOC—(CHR$^1$)—NH$_2$ (VIIc)

=t-ButOOC—(CH$_2$)$_2$—NH$_2$ (VIId)

wherein $R^1$ is as above defined, according to methods well known in the art.

Compounds (IVc) are known in the art or can be prepared from known compounds by known methods such as for example from the corresponding alcohols of formula (VIIIa),

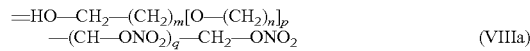
(VIIIa)

wherein m, n, p and q are as above defined, by oxidation with known agents such as TEMPO or Ruthenium (IV) oxide/Sodium periodate.

2) The compound of formula (I) wherein R is —H and Ra is selected from the groups A1), A2) or A3):

A1): —(CHR$^1$)—NH—(C=O)—(CH$_2$)$_m$—[O—(CH$_2$)$_n$]$_p$—(CH—ONO$_2$)$_q$—CH$_2$—ONO$_2$

A2): —(CH$_2$)$_2$—NH—(C=O)—(CH$_2$)$_m$—[O—(CH$_2$)$_n$]$_p$—(CH—ONO$_2$)$_q$—CH$_2$—ONO$_2$

A3): —(CH$_2$)$_m$—[O—(CH$_2$)$_n$]$_p$—(CH—ONO$_2$)$_q$—CH$_2$—ONO$_2$ wherein:

$R^1$, m, n, p and q are as above defined;

can be prepared by deprotecting an allyl or isoprenyl ester of formula (IX), wherein Ra is as above defined and Y is —H or —CH$_3$, with methods known in the literature (see for example: T. W. Greene, P. G. M. Wuts "Protective groups in organic Synthesis", 4th edition, J. Wiley & Sons, New York, 2006) and eventually reacting the deprotected compound in MeOH as already described for compound (II):

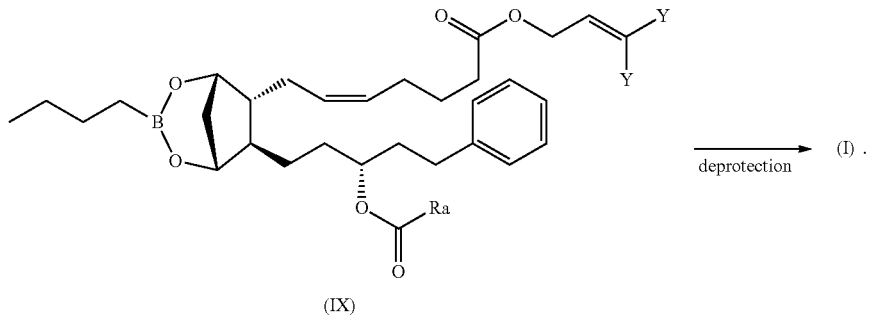
(IX)

Compounds of formula (IX), wherein Ra is as above defined, can be generally prepared by reacting a compound of formula (X) with compounds of formula (IVa-c):

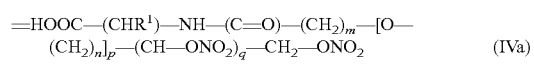
(IVa)

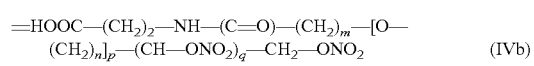
(IVb)

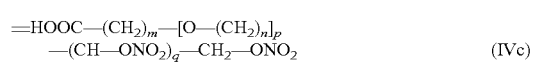
(IVc)

as depicted in the below reported scheme:

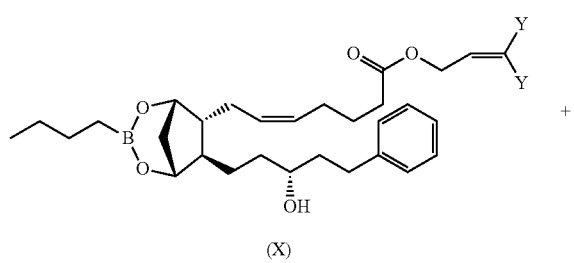
(X)

-continued

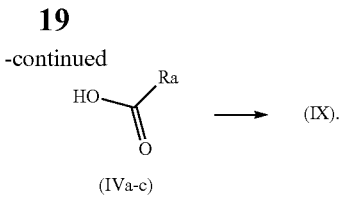

The reaction is carried out in a aprotic polar/non polar solvent such as THF, DMF or CH$_2$Cl$_2$, in presence of DCC, EDAC, HBTU, HATU or other coupling reagents, in presence of catalytic amount of DMAP at temperature ranging from 0° C. to 80° C.

Alternatively, the compounds of formula (IX) can be generally prepared by reacting a compound of formula (X) with compounds of formula (Va-c):

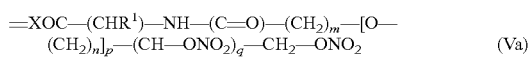 (Va)

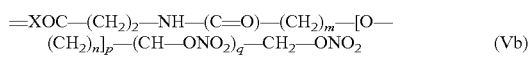 (Vb)

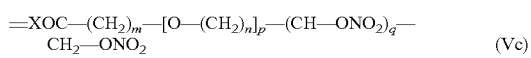 (Vc)

wherein X is —Cl, p-nitrophenoxy, pentafluorophenoxy or 2,5-pyrrolidinedione, 1-oxy as depicted in the below reported scheme:

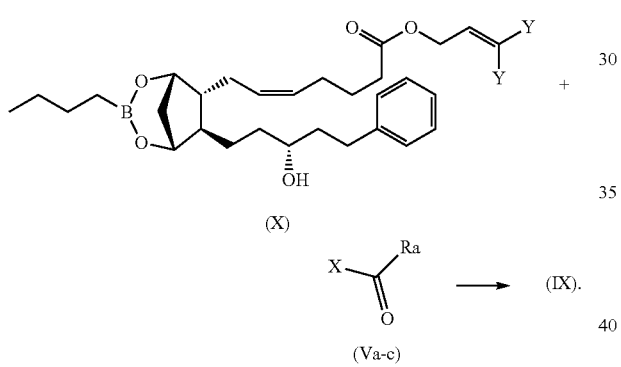

When X=—Cl, the reaction is carried out in presence of a base such as DMAP, pyridine or triethylamine or K$_2$CO$_3$, Cs$_2$CO$_3$ in an aprotic/non polar solvent such as THF, DMF or CH$_2$Cl$_2$, at a temperature ranging from −20° C. to 60° C.

When X is selected from p-nitrophenoxy, pentafluorophenoxy or 2,5-pyrrolidinedione, 1-oxy, the reaction is carried out in a aprotic polar/non polar solvent such as THF, DMF or CH$_2$Cl$_2$, in presence of DMAP at temperature ranging from 0° C. to 80° C.

The compound of formula (X) can be prepared as already described for analogous compound (III) by reacting a compound (XI) with butylboronic acid following a general procedure reported in Organic Syntheses, Coll. Vol. 10, p. 613 (2004).

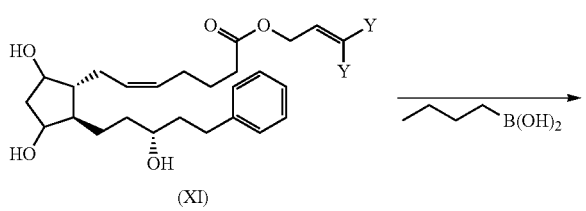

-continued

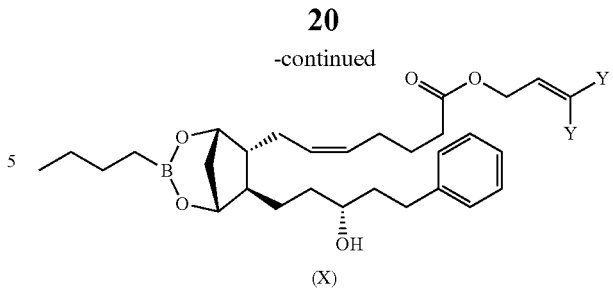

Compound (XI) can be prepared from latanoprost acid by known methods, as by reacting latanoprost acid with allyl chloride (Y=H) or 2-Butene, 1-chloro-3-methyl-(Y=CH$_3$) in the presence of an organic or inorganic base following general procedures known in the literature (see for example: T. W. Greene, P. G. M. Wuts "Protective groups in organic Synthesis", 4th edition, J. Wiley & Sons, New York, 2006).

Alternatively the compound of formula (I) wherein R is —H and Ra is selected from the groups A1), A2) or A3):

A1): —(CHR$^1$)—NH—(C=O)—(CH$_2$)$_m$—[O—(CH$_2$)$_n$]$_p$—(CH—ONO$_2$)$_q$—CH$_2$—ONO$_2$

A2): —(CH$_2$)$_2$—NH—(C=O)—(CH$_2$)$_m$—[O—(CH$_2$)$_n$]$_p$—(CH—ONO$_2$)$_q$—CH$_2$—ONO$_2$

A3): —(CH$_2$)$_m$—[O—(CH$_2$)$_n$]$_p$—(CH—ONO$_2$)$_q$—CH$_2$—ONO$_2$ wherein:

R$^1$, m, n, p and q are as above defined;

can be prepared by reacting compound (XII) with MeOH as already described for compound (II):

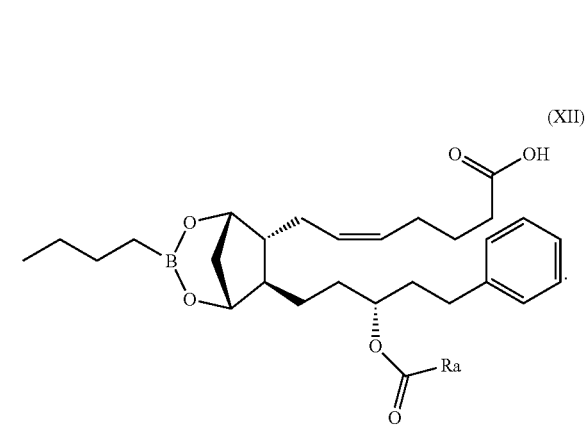

Compounds of formula (XII), wherein Ra is as above defined, can be generally prepared by reacting a compound of formula (XIII) with compounds of formula (Va-c):

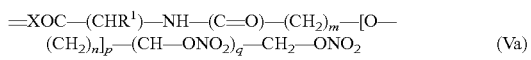 (Va)

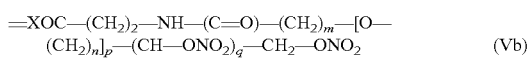 (Vb)

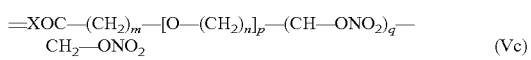 (Vc)

wherein X is —Cl, p-nitrophenoxy, pentafluorophenoxy or 2,5-pyrrolidinedione, 1-oxy as depicted in the below reported scheme:

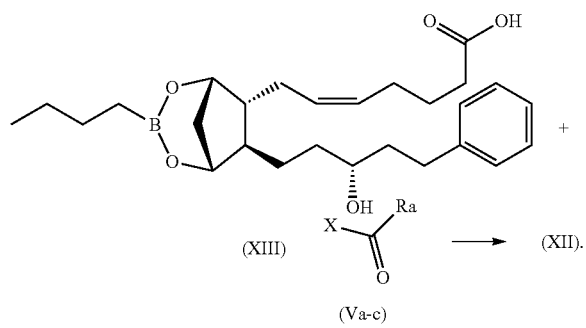

When X=—Cl, the reaction is carried out in presence of a base such as DMAP, pyridine or triethylamine or $K_2CO_3$, $Cs_2CO_3$ in an aprotic/non polar solvent such as THF, DMF or $CH_2Cl_2$, at a temperature ranging from −20° C. to 60° C.

When X is selected from p-nitrophenoxy, pentafluorophenoxy or 2,5-pyrrolidinedione, 1-oxy, the reaction is carried out in a aprotic polar/non polar solvent such as THF, DMF or $CH_2Cl_2$, in presence of DMAP at temperature ranging from 0° C. to 80° C.

The compound of formula (XIII) can be prepared as already described for analogous compound (III) by reacting latanoprost acid (XIV) with butylboronic acid following a general procedure reported in Organic Syntheses, Coll. Vol. 10, p. 613 (2004).

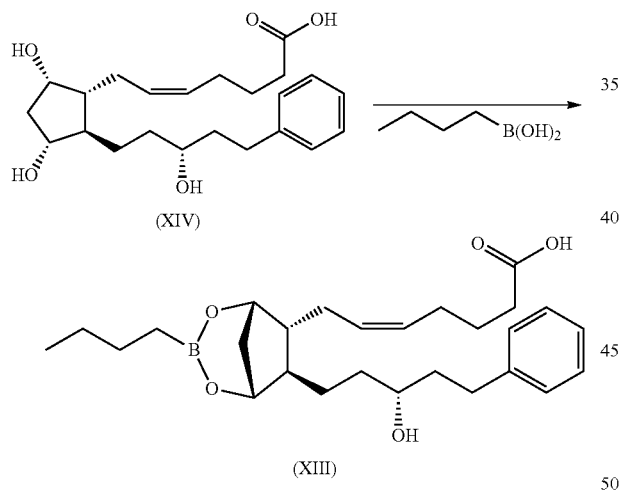

The invention claimed is:
1. A compound of formula (I) or salts thereof

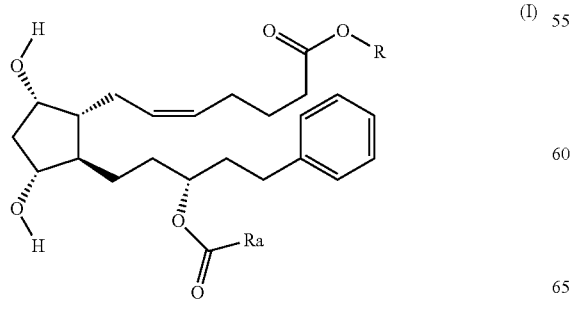

wherein
R is —CH(CH3)2 or H;
Ra is selected from
A1): —(CHR1)-NH—(C=O)—(CH2)m-[O—(CH2)n]p-(CH—ONO2)q-CH2-ONO2
A2): —(CH2)2-NH—(C=O)—(CH2)m-[O—(CH2)n]p-(CH—ONO2)q-CH2-ONO2
A3): —(CH2)m-[O—(CH2)n]p-(CH—ONO2)q-CH2-ONO2
wherein
R1 is —H or —CH3,
p is 1 or 0,
q is 1 or 0,
m is an integer ranging from 1 to 10;
n is an integer ranging from 1 to 6.

2. A compound of formula (I) according to claim 1, wherein
R is —CH(CH3)2 and
Ra is A1): —(CHR1)-NH—(C=O)—(CH2)m-[O—(CH2)n]p-(CH—ONO2)q-CH2-ONO2
wherein
R1 is —H or —CH3,
p is 1 or 0,
q is 1 or 0,
m is an integer ranging from 1 to 10;
n is an integer ranging from 1 to 6.

3. A compound of formula (I) according to claim 2, wherein Ra is selected from the following group of linkers:

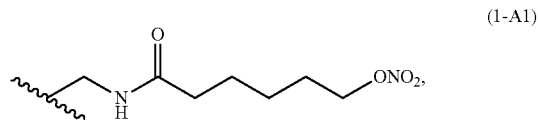
(1-A1)

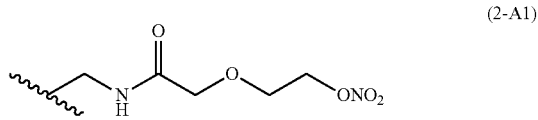
(2-A1)

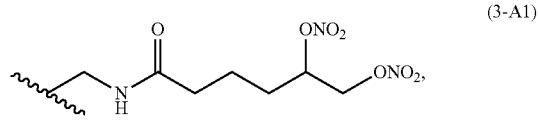
(3-A1)

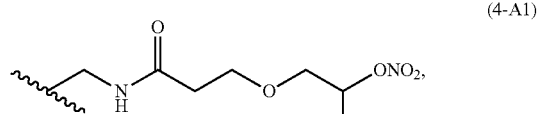
(4-A1)

(5-A1)

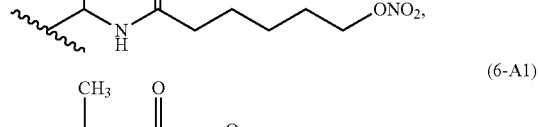
(6-A1)

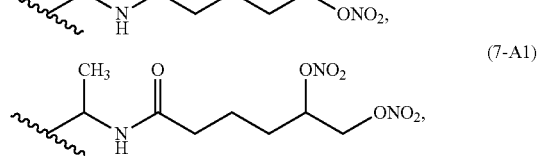
(7-A1)

(8-A1)

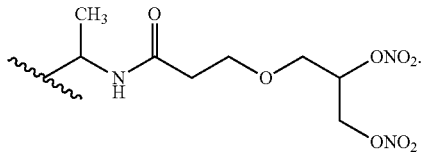

4. A compound of formula (I) according to claim 1, wherein R is —CH(CH3)2 and
Ra is A2): —(CH2)2-NH—(C=O)—(CH2)m-[O—(CH2)n]p-(CH—ONO2)q-CH2-ONO2
wherein
p is 1 or 0,
q is 1 or 0,
m is an integer ranging from 1 to 10;
n is an integer ranging from 1 to 6.

5. A compound of formula (I) according to claim 4, wherein Ra is selected from the following group of linkers:

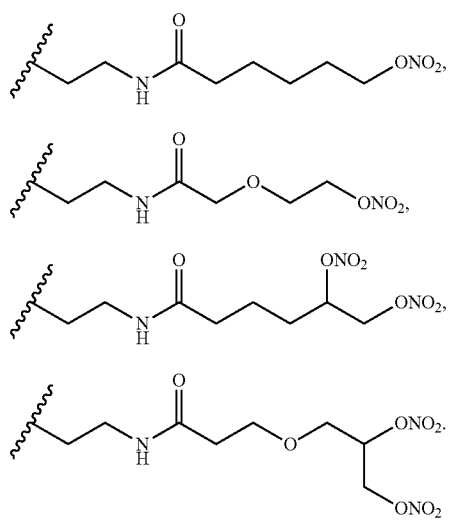

(1-A2)

(2-A2)

(3-A2)

(4-A2)

6. A compound of formula (I) according to claim 1, wherein R is —CH(CH3)2 and
Ra is A3): —(CH2)m-[O—(CH2)n]p-(CH—ONO2)q-CH2-ONO2
wherein
p is 1 or 0,
q is 1 or 0,
m is an integer ranging from 1 to 10;
n is an integer ranging from 1 to 6.

7. A compound according to claim 6, wherein Ra is selected from the following group of linkers:

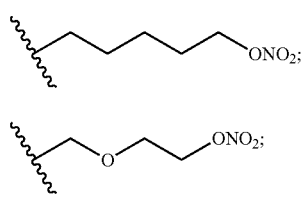

(1-A3)

(2-A3)

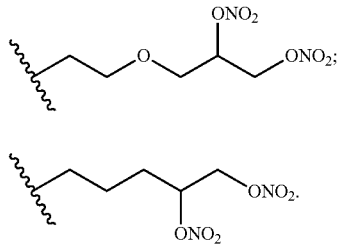

(3-A3)

(4-A3)

8. A compound of formula (I) according to claim 1, wherein R is —H.

9. A compound of formula (I) according to claim 8, wherein Ra is selected from the following group of linkers having structure A1:

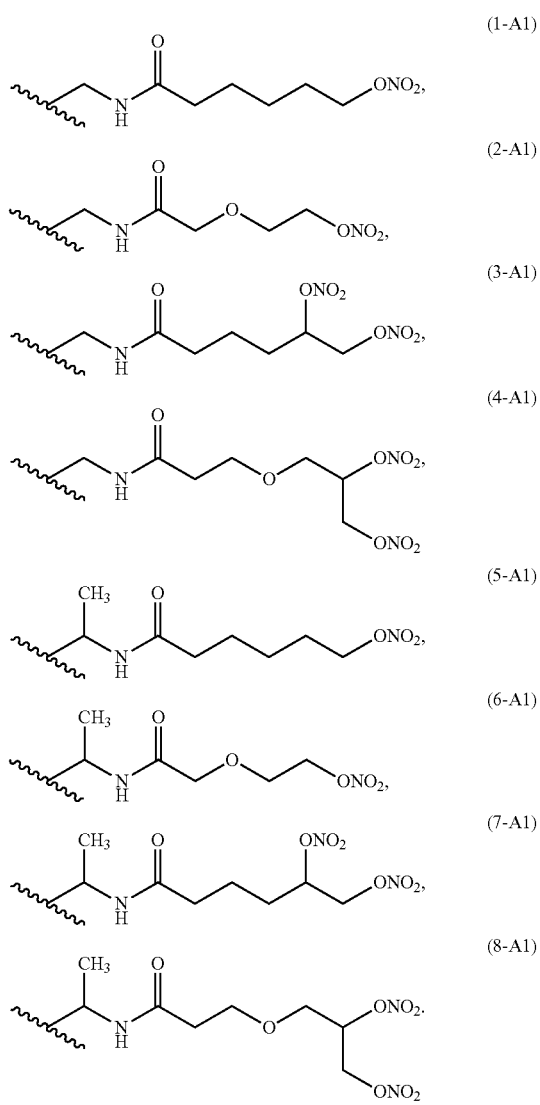

(1-A1)

(2-A1)

(3-A1)

(4-A1)

(5-A1)

(6-A1)

(7-A1)

(8-A1)

10. A compound of formula (I) according to claim 8, wherein Ra is selected from the following group of linkers having structure A2:

11. A compound of formula (I) according to claim 8, wherein Ra is selected from the following group of linkers having structure A3:

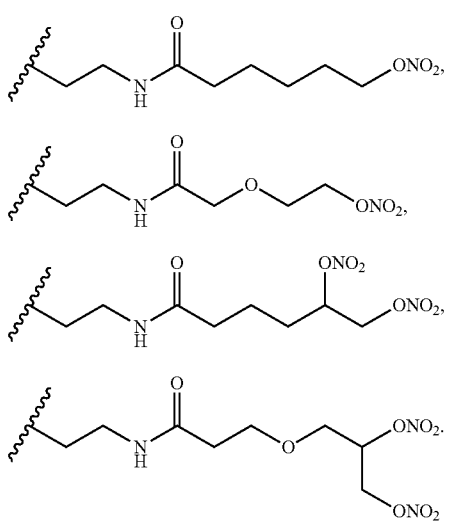

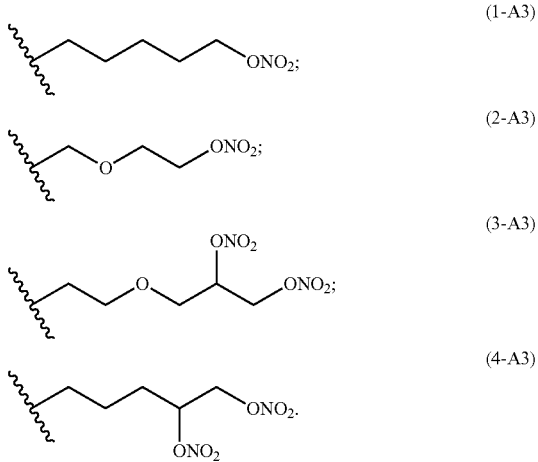

12. A compound of formula (I) according to claim 1, selected from the following group of compounds:

(Z)-isopropyl 7-((1R,2R,3R,5S)-3,5-dihydroxy-2-((R)-3-(3-(6-(nitrooxy)hexanamido) propanoyloxy)-5-phenylpentyl)cyclopentyl)hept-5-enoate (Compound (1));

(Z)-isopropyl 7-((1R,2R,3R,5S)-2-((3R)-3-(3-(5,6-bis(nitrooxy)hexanamido) propanoyloxy)-5-phenylpentyl)-3,5-dihydroxycyclopentyl)hept-5-enoate (Compound (2));

(Z)-isopropyl 7-((1R,2R,3R,5S)-3,5-dihydroxy-2-((R)-3-(3-(2-(2-(nitrooxy)ethoxy)acetamido)propanoyloxy)-5-phenylpentyl)cyclopentyl)hept-5-enoate (Compound (3));

(Z)-isopropyl 7-((1R,2R,3R,5S)-2-((3R)-3-(3-(2,3-bis(nitrooxy)propoxy) propanamido)propanoyloxy)-5-phenylpentyl)-3,5-dihydroxycyclopentyl)hept-5-enoate (Compound (4));

(Z)-isopropyl 7-((1R,2R,3R,5S)-3,5-dihydroxy-2-((R)-3-(2-(6-(nitrooxy)hexanamido)acetoxy)-5-phenylpentyl)cyclopentyl)hept-5-enoate (Compound (5));

(Z)-isopropyl 7-((1R,2R,3R,5S)-2-((3R)-3-(2-(5,6-bis(nitrooxy)hexanamido)acetoxy)-5-phenylpentyl)-3,5-dihydroxycyclopentyl)hept-5-enoate (Compound (6));

(Z)-isopropyl 7-((1R,2R,3R,5S)-3,5-dihydroxy-2-((R)-3-(2-(2-(2-(nitrooxy)ethoxy) acetamido)acetoxy)-5-phenylpentyl)cyclopentyl)hept-5-enoate (Compound (7));

(Z)-isopropyl 7-((1R,2R,3R,5S)-2-((3R)-3-(2-(3-(2,3-bis(nitrooxy)propoxy) propanamido)acetoxy)-5-phenylpentyl)-3,5-dihydroxycyclopentyl)hept-5-enoate (Compound (8));

(Z)-isopropyl 7-((1R,2R,3R,5S)-3,5-dihydroxy-2-((R)-3-(6-(nitrooxy)hexanoyloxy)-5-phenylpentyl)cyclopentyl)hept-5-enoate (Compound (9));

(Z)-isopropyl 7-((1R,2R,3R,5S)-2-((3R)-3-(5,6-bis(nitrooxy)hexanoyloxy)-5-phenylpentyl)-3,5-dihydroxycyclopentyl)hept-5-enoate (Compound (10));

(Z)-isopropyl 7-((1R,2R,3R,5S)-3,5-dihydroxy-2-((R)-3-(2-(2-(nitrooxy)ethoxy) acetoxy)-5-phenylpentyl)cyclopentyl)hept-5-enoate (Compound (11));

(Z)-isopropyl 7-((1R,2R,3R,5S)-2-((3R)-3-(3-(2,3-bis(nitrooxy)propoxy)propanoyloxy)-5-phenylpentyl)-3,5-dihydroxycyclopentyl)hept-5-enoate (Compound (12)).

13. A compound of formula (I) according to claim 1, for use as medicament.

14. A compound of formula (I) according to claim 1, for use in the treatment of ocular hypertension.

15. A compound of formula (I) according to claim 1, for use in the treatment of ocular hypertension or glaucoma.

16. A compound of formula (I) for the use according to claim 15, wherein glaucoma is primary open angle glaucoma, normal intraocular tension glaucoma, pseudoexfoliation glaucoma, acute angle-closure glaucoma or chronic closed angle glaucoma.

17. A topical ocular pharmaceutical composition comprising a compound of formula (I) according to claim 1 as active principle and a pharmaceutically acceptable excipient or a combination of excipients.

18. A composition comprising a compound of formula (I) according to claim 1 and at least another active agent selected from the following classes of drugs:

Beta-adrenergic antagonists, Adrenergic agonists, Alpha2-selective adrenergic agonists, Carbonic Anhydrase Inhibitors, Cholinergic agonists, Cholinesterase inhibitors.

19. A composition according to claim 18 for use in the treatment of ocular hypertension or glaucoma.

* * * * *